US012624374B1

(12) United States Patent
Leal et al.

(10) Patent No.: US 12,624,374 B1
(45) **Date of Patent: *May 12, 2026**

(54) PROCESSES USING NUCLEOSIDE TRIPHOSPHATES WITH STABLE AMINOXY GROUPS

(71) Applicant: Firebird Biomolecular Sciences, Alachua, FL (US)

(72) Inventors: Nicole A. Leal, Gainesville, FL (US); Steven A Benner, Gainesville, FL (US)

(73) Assignee: FIREBIRD BIOMOLECULAR SCIENCES, Alachua, FL (US)

( * ) Notice: Subject to any disclaimer, the term of this patent is extended or adjusted under 35 U.S.C. 154(b) by 1143 days.

This patent is subject to a terminal disclaimer.

(21) Appl. No.: 17/473,513

(22) Filed: Sep. 13, 2021

Related U.S. Application Data

(63) Continuation-in-part of application No. 16/887,951, filed on May 29, 2020, now Pat. No. 11,850,258, and a continuation-in-part of application No. 16/679,501, filed on Nov. 11, 2019, now Pat. No. 11,117,922, and a continuation-in-part of application No. 16/679,887, filed on Nov. 11, 2019, now abandoned, said application No. 16/679,501 is a continuation-in-part of application No. 15/460,475, filed on Mar. 16, 2017, now Pat. No. 10,472,383, and a continuation-in-part of application No. 15/786,086, filed on Oct. 17, 2017, now Pat. No. 10,654,841, which is a continuation-in-part of application No. 15/475,694, filed on Mar. 31, 2017, now abandoned.

(51) Int. Cl.

| | |
|---|---|
| ***C07H 21/00*** | (2006.01) |
| ***C12P 19/34*** | (2006.01) |
| *C07H 21/04* | (2006.01) |

(52) U.S. Cl.
CPC .............. *C12P 19/34* (2013.01); *C07H 21/04* (2013.01)

(58) Field of Classification Search
CPC .......... C07H 21/00; C07H 21/04; C07H 1/00; C07H 19/04; C12Y 207/07031; C12Y 207/07
See application file for complete search history.

(56) References Cited

PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*

* cited by examiner

*Primary Examiner* — Tekchand Saidha
*Assistant Examiner* — Mohammad Y Meah
(74) *Attorney, Agent, or Firm* — SALIWANCHIK, LLOYD & EISENSCHENK

(57) ABSTRACT

This invention claims processes that append a single nucleotide having a 3'-$ONH_2$ moiety to the 3'-ends of an oligonucleotide primer using 3'-deoxynucleoside triphosphates that have, instead of a 3'-OH moiety, a 3'-$ONH_2$ moiety, where the nucleotides contain both standard and non-standard nucleobases, and where as a key claim limitation, substantially no hydroxylamine is present in the solutions used in the claimed processes.

17 Claims, 10 Drawing Sheets

Figure 1:
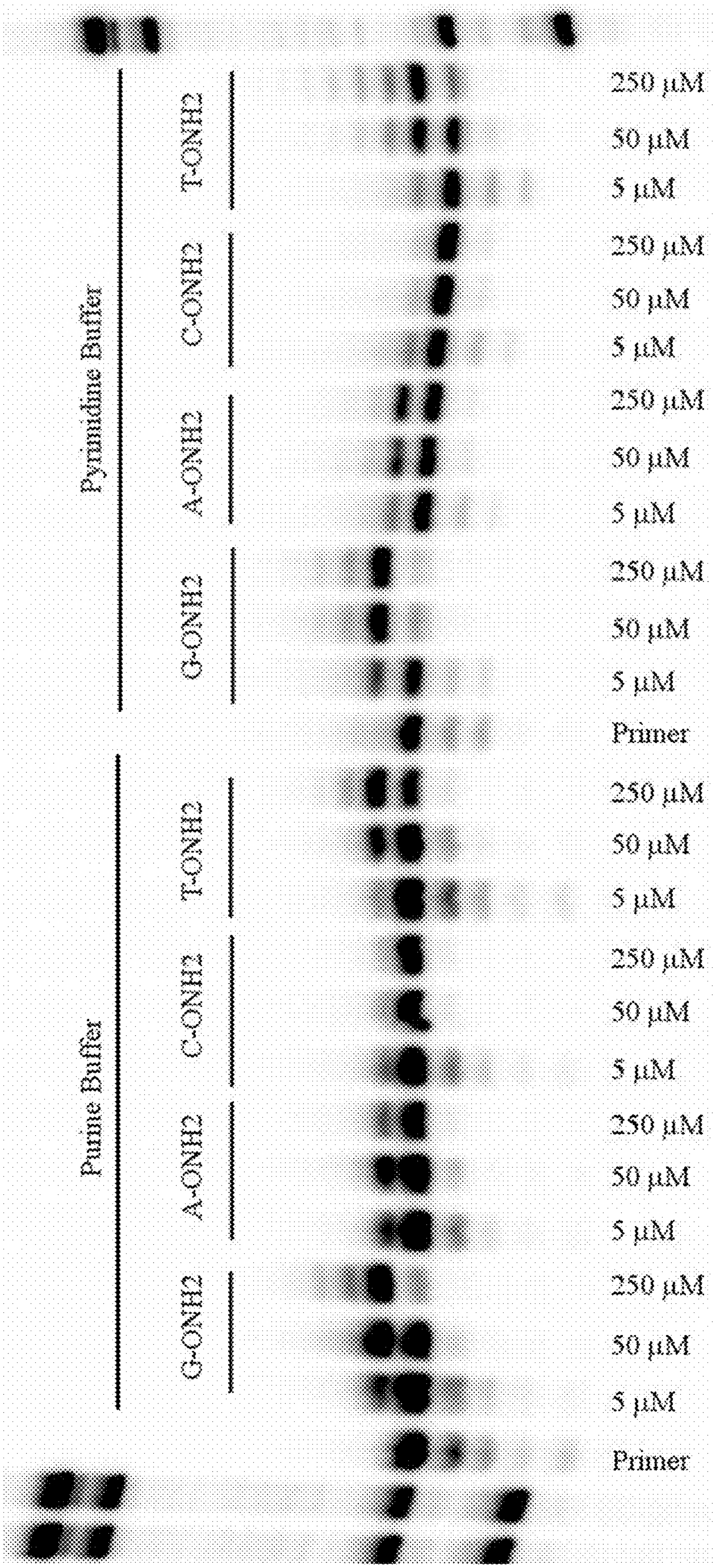

Specification includes a Sequence Listing.

PROCESSES USING NUCLEOSIDE TRIPHOSPHATES WITH STABLE AMINOXY GROUPS

CROSS REFERENCE TO RELATED APPLICATIONS

This is a continuation-in-part of U.S. patent application Ser. No. 16/679,501, filed 11 Nov. 2019, currently pending, which was a continuation in part of U.S. patent application Ser. No. 15/460,475, filed 16 Mar. 2017 now U.S. patent Ser. No. 10/472,383, and U.S. patent application Ser. No. 15/786,086, filed 17 Oct. 2017 now U.S. patent Ser. No. 10/654,841. U.S. patent application Ser. No. 15/786,086 is a continuation in part of U.S. patent application Ser. No. 15/475,694, filed 31 Mar. 2017, and now abandoned. This is also a continuation-in-part of U.S. patent application Ser. No. 16/887,951, filed 29 May 2020, pending. This is also a continuation-in-part of U.S. patent application Ser. No. 16/679,887, filed 29 May 2020, pending.

STATEMENT OF RIGHTS TO INVENTIONS MADE UNDER FEDERALLY-SPONSORED RESEARCH

This invention was made with government support under R41GM119494 awarded by the National Institutes of General Medical Sciences. The government has certain rights in the invention.

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

This invention relates to the field of nucleic acid chemistry, and more specifically to DNA and DNA-like molecules that have a 3'-$ONH_2$ group rather than the 3'-OH group that is found in standard DNA, DNA with non-standard nucleobases, and DNA-like molecules (collectively hereinafter "DNA"). Still more specifically, this invention relates to enzymatic processes that attach, to the end of a standard DNA, RNA, and/or DNA-like or RNA-like molecule, a nucleotide that has its 3'-OH group substantially completely replaced by a 3'-$ONH_2$ group, using a triphosphate analog in an aqueous solution that lacks hydroxylamine. This invention also relates to processes where a DNA polymerase, a reverse transcriptase, a polynucleotide polymerase (e.g. polyA polymerase or polyU polymerase [Church, G. M., Wiegand, D. J., Kohnan, R. E., Kuru, E., Ricttichier, J., Conway, N. (2020) Enzymatic RNA Synthesis, WO/2020/077227 A2][Heinisch, T., Champion, E., Sune, E., Soskine, M. (2021) Template Free Enzymatic synthesis of polynucleotides using Poly(A) and Poly (U) polymerases, WO/2021/018919], or a terminal deoxynucleotide transferase uses a nucleoside triphosphate having a 3'-$ONH_2$ group to add a 3'-aminoxy-2',3'-dideoxynucleotide to the 3'-end of a DNA or DNA-like molecule.

(2) Description of Related Art

Well-known in the art are useful processes that require that the enzymatic extension of a DNA, DNA-like, or RNA oligonucleotide (hereinafter a primer) be terminated after introduction of just a single nucleotide at the 3'-end. This extension may be templated, as in the primer-extension processes that are catalyzed by DNA polymerases, RNA polymerases, or reverse transcriptases. Here, successful termination after the addition of just one nucleotide underlies many DNA sequencing architectures, especially those known to use "cyclic reversible termination". Termination of template-guided extension after the addition of a single nucleotide is frequently achieved by contacting the enzyme to analog of a nucleoside triphosphate where the nucleoside has been altered so as to no longer have a free 3'-hydroxyl group.

Also well known in the art are processes where extension in not templated. Here, a common enzyme to catalyze the process is a terminal deoxynucleotide transferase (TdT). Termination after addition of just a single nucleotide is used in many DNA synthesizing architectures.

Well known among these analogs are triphosphates where the 3'-hydroxyl group is replaced by a hydrogen atom to generate 2',3'-dideoxynucleoside triphosphates. These are substrates for many polymerases, including many modified polymerases. In forms that carry side chains carrying reporter groups, these have long been used in DNA sequencing processes. Since no convenient method is available to replace the 3'-H by a 3'-OH group on an oligonucleotide, the termination of the oligonucleotide extension process in the presence of a 2',3'-dideoxynucleoside triphosphate analog is said to be irreversible.

Other nucleoside and oligonucleotide derivatives lacking the standard 3'-OH have functionality that can later be converted to a 3'-OH group under conditions that do not damage oligonucleotides. This allows template-directed primer extension to be terminated "reversibly".

For example, various patents, including U.S. Pat. Nos. 7,544,794, 8,034,923, and 8,212,020, disclosed that a 3'-O—$NH_2$ group may be used a reversibly terminating moiety. These are referred to as 3'-aminoxy-2',3'-dideoxynucleosides, -tides, and triphosphates. After a nucleotide having a 3'-O—$NH_2$ group is added to the 3'-end of an oligonucleotide primer, further polymerase-catalyzed extension cannot occur.

This terminating 3'-O—$NH_2$ group may not be removed, allowing its reactivity to be used for a variety of purposes. For example, the 3'-O—$NH_2$ group can react with another molecule that carries an aldehyde or ketone moiety to form useful oximes.

However, if the appropriate reagents are added, the nitrogen-oxygen bond of the 3'-O—$NH_2$ group can be cleaved, thereby converting the 3'-$ONH_2$ group to a 3'-OH group. Once converted, enzymatic extension can proceed. U.S. Pat. Nos. 7,544,792 and 8,212,020 did not provide a practical reagent for cleaving the nitrogen-oxygen bond in the 3'-O—$NH_2$ unit in an oligonucleotide to generate an extendable 3'-OH group, U.S. Pat. No. 8,034,923 did. U.S. Pat. No. 8,034,923 taught that the nitrogen-oxygen bond in the 3'-O—$NH_2$ unit could be cleaved by an aqueous solution of sodium nitrite buffered to a pH of near six. The product of that cleavage reaction is a 3'-OH group.

The art is, however, defective when it concerns the 3'-O—$NH_2$ unit. For the process using this unit to be useful for both DNA sequencing and for enzyme-based DNA synthesis, the triphosphate must be substantially free of contaminant triphosphate having a free 3'-OH group, where "substantially" means in this context less than 0.1%. Preferably, the level of contaminating 3'-OH group is still lower. Otherwise, the enzyme adds a second nucleotide to the DNA molecule that serves as a primer to give an "n+2" product; the n+1 product arises from the desired addition of just one nucleotide. In enzyme synthesis architectures using TdT, this leads to products that are contaminated with analogous products and have a single nucleotide inserted at undesired positions throughout the synthetic product. In enzyme sequencing architectures, n+2 products lead to confusion and sequencing reads.

Figure 10:
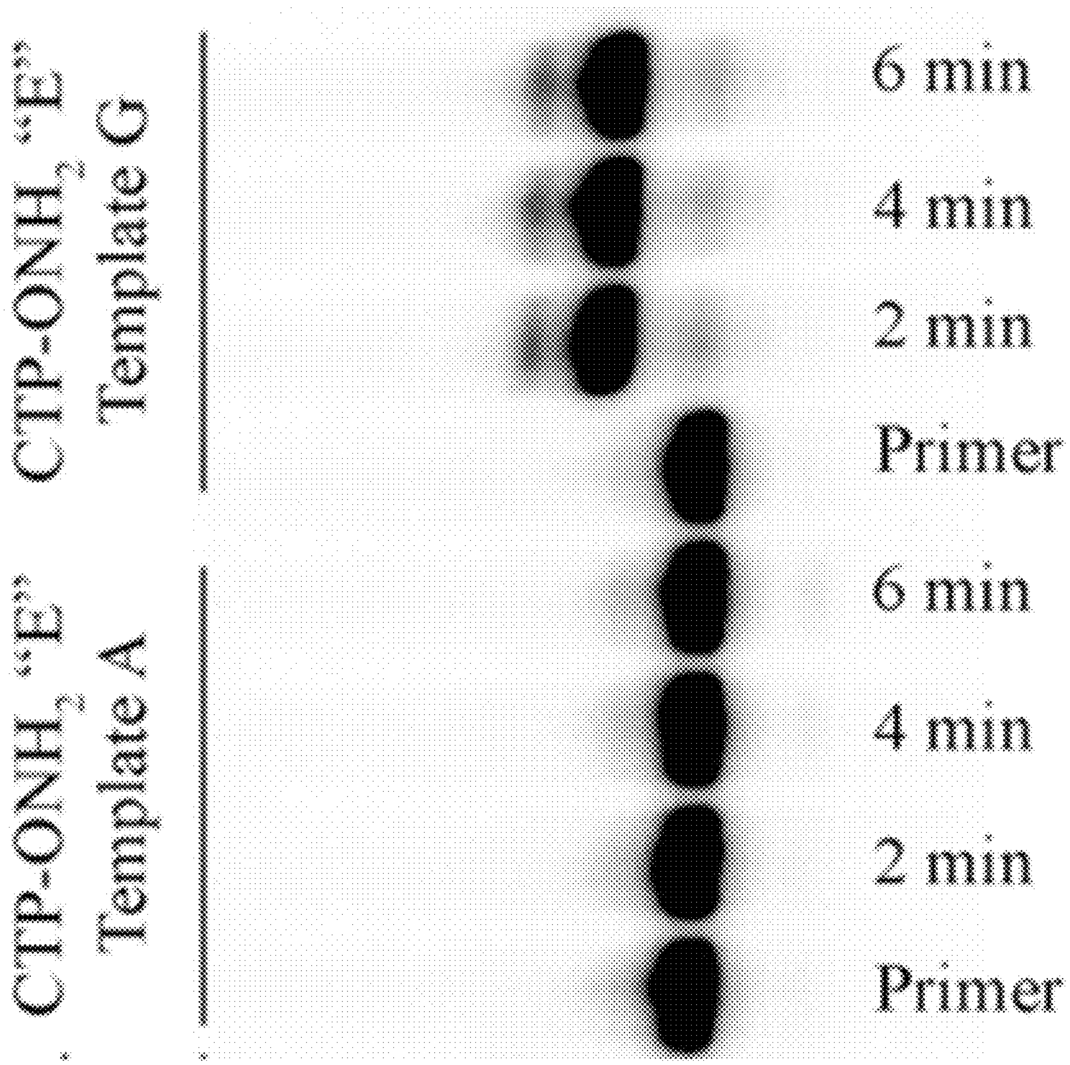

The significance of this defect should not be overlooked. It is visible in all experiments seen with the triphosphates present in the art prior to the priority date of the instant application. An example is shown in FIG. 10. Here, 0.1% contaminant generates about 3% n+2 product, reflecting the fact that the terminal transferase disproportionately prefers the 3'-OH triphosphate over the more abundant 3'-$ONH_2$ triphosphate.

As taught in U.S. patent application Ser. No. 15/460,475 (Benner, S. A. (2017) Nucleoside Triphosphates with Stable Aminoxy Groups. Filed 16 Mar. 2017), for which this is a continuation in part and whose disclosure is incorporated in its entirety herein by reference, the processes disclosed in the prior art for making triphosphates with a 3'-O—$NH_2$ unit did not provide triphosphates sufficiently free of triphosphates having 3'-OH groups for the processes to have their full utility. Specifically, all the preparations disclosed, intrinsically because of the method of their preparation, contained small but substantial amounts of 3'-nucleoside triphosphates having unblocked 3'-OH groups, here defined as 0.1% or greater. Thus, use of these in template reactions frequently did not lead to termination of all oligonucleotide chains.

BRIEF SUMMARY OF THE INVENTION

As noted in a declaration submitted during the prosecution of patent application Ser. No. 15/460,475, a solid phase process was invented that allowed triphosphate having a 3'-$ONH_2$ group to be synthesized substantially free of triphosphates having a 3'-OH group. This process is based on the unexpected discovery that this outcome required strict exclusion of hydroxylamine from both the manufacturing and use processes of these triphosphates. This process is covered by allowed claims in patent application Ser. No. 15/460,475.

Further, patent application Ser. No. 15/460,475 disclosed compositions of matter that are nucleoside triphosphates of both standard and nonstandard nucleosides having 3'-$ONH_2$ groups that are substantially free of triphosphates having a 3'-OH groups. These compositions are also covered by allowed claims in patent application Ser. No. 15/460,475.

The instant invention covers enzymatic processes that use compositions of matter covered by allowed claims in patent application Ser. No. 15/460,475, which are produced by a process covered by allowed claims in patent application Ser. No. 15/460,475. Various of these processes were disclosed in application Ser. No. 15/786,086, whose disclosure is also incorporated herein in its entirety by reference. The instant invention covers enzymatic processes that use compositions of matter covered by allowed claims in patent application Ser. No. 16/887,951, whose disclosure is also incorporated herein in its entirety by reference.

BRIEF DESCRIPTION OF THE SEVERAL VIEWS OF THE DRAWING(S)

FIG. 1. A polyacrylamide gel electrophoresis (PAGE) image showing the addition by TdT of a single nucleotide carrying a 3'-$ONH_2$ group in two different buffers to a primer carrying a 5'-phosphorus-32 label. External bands are ladders. The concentrations of the aminoxytriphosphates are shown below each lane, for the aminoxytriphosphate indicated at the top of each lane.

Figure 2:
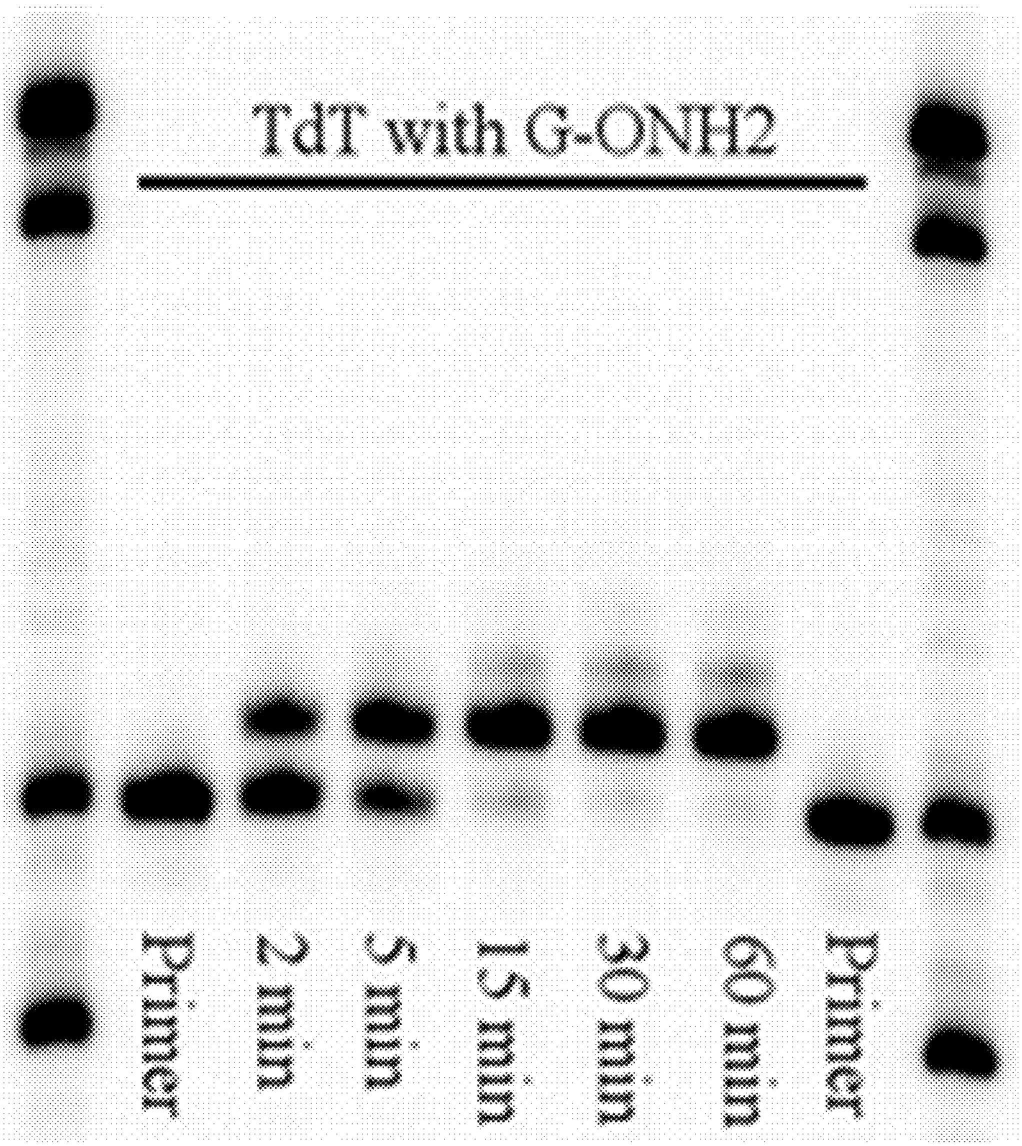

FIG. 2: PAGE (16%) is a time course of GTP-$ONH_2$ incorporation using TdT. Addition of a single nucleotide is complete at ca. 15 minutes. This preparation contains substantial amounts of dGTP having a free 3'-OH group, as indicated by the second shadow band.

Figure 3:
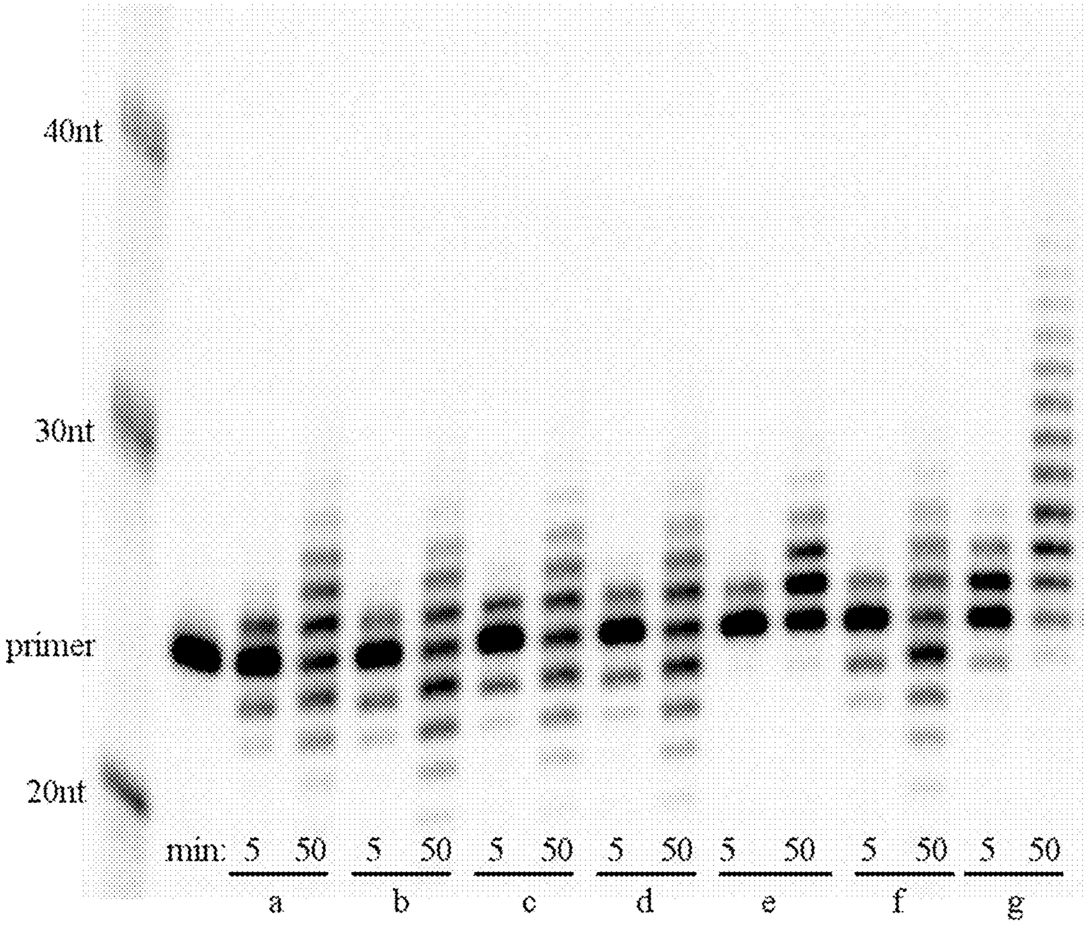

FIG. 3. PAGE (20%) of aminoxy samples tested in terminal transferase reaction to extend a 5'-radiolabeled primer. Lanes labeled a through g have different triphosphates as described in the text; incubation times are 5 and 50 minutes, as indicated.

Figure 4:
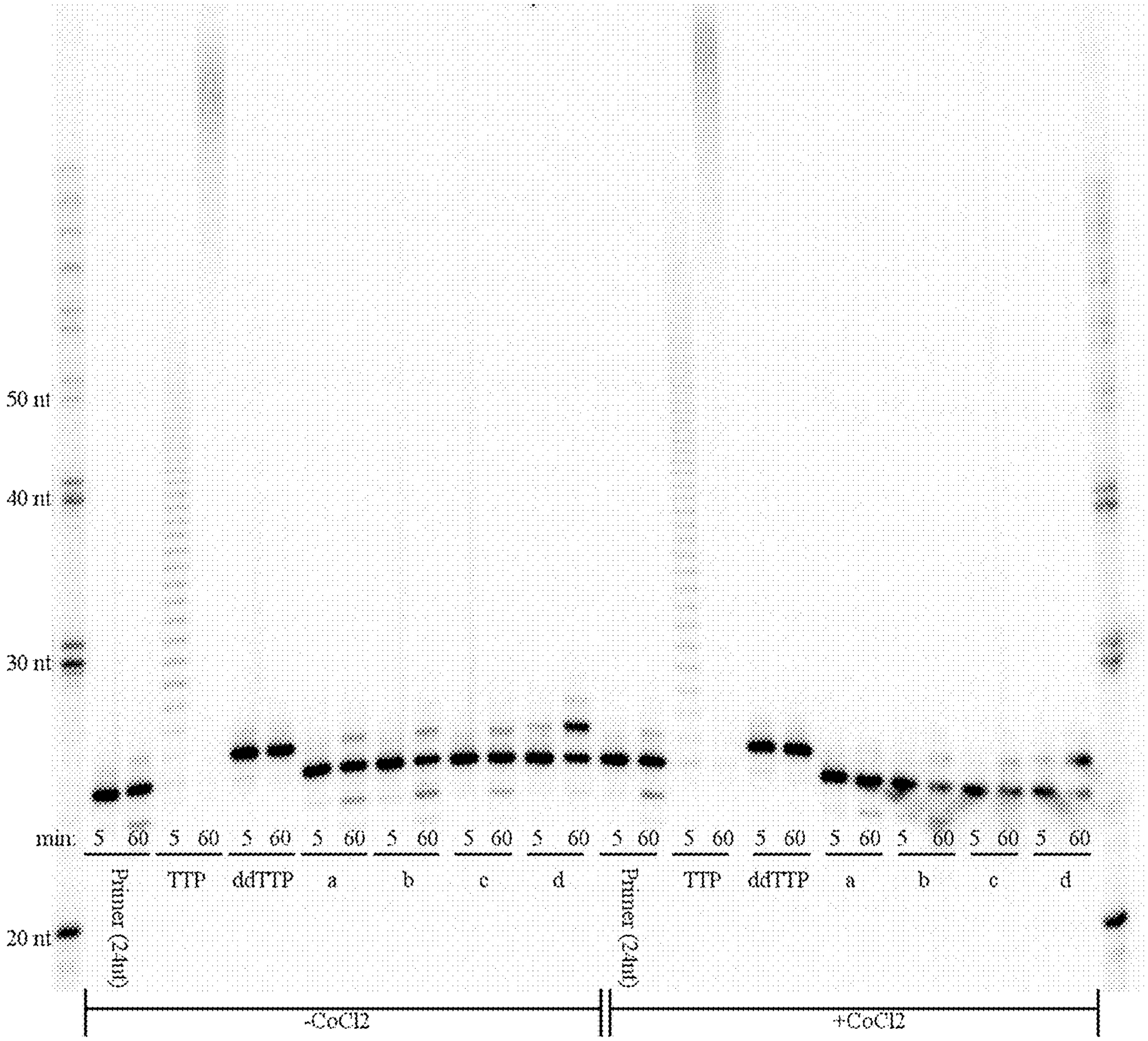

FIG. 4. PAGE (20%) of control and aminoxy triphosphates prepared as taught in U.S. patent application Ser. No. 15/460,475 tested in a terminal transferase reaction in two different buffers. This data set shows no significant impact of the presence of divalent cobalt cation in the incubation buffer.

Figure 5:
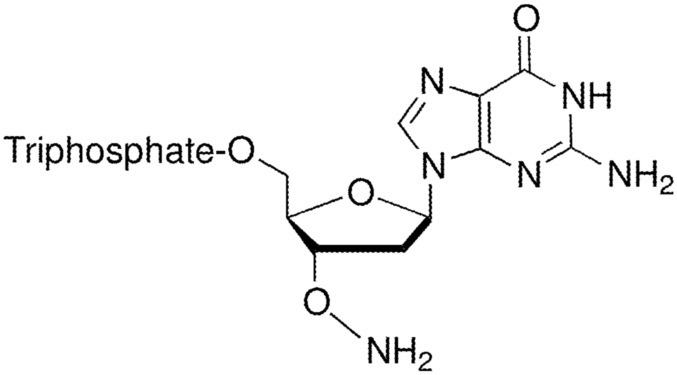
Figure 5:
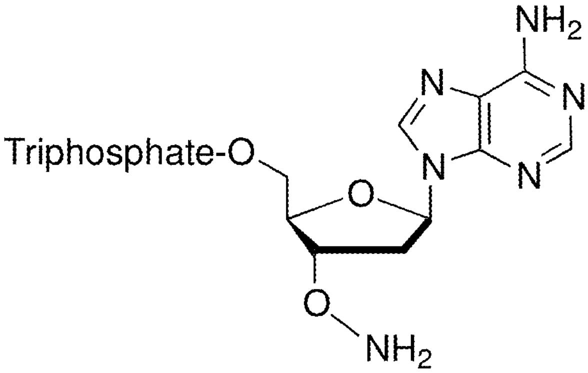
Figure 5:
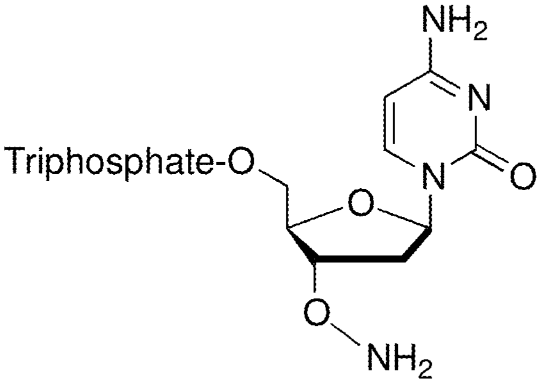
Figure 5:
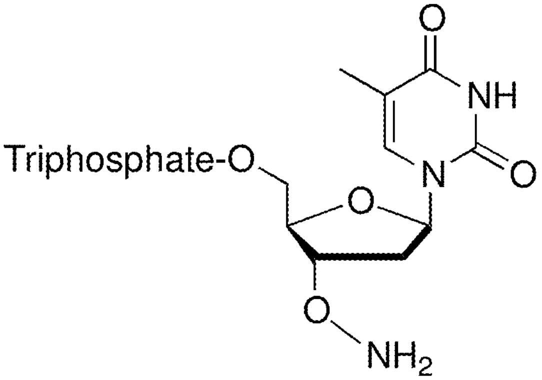

FIG. 5. Structures of the standard 3'-aminoxytriphosphates of the instant invention.

Figure 6:
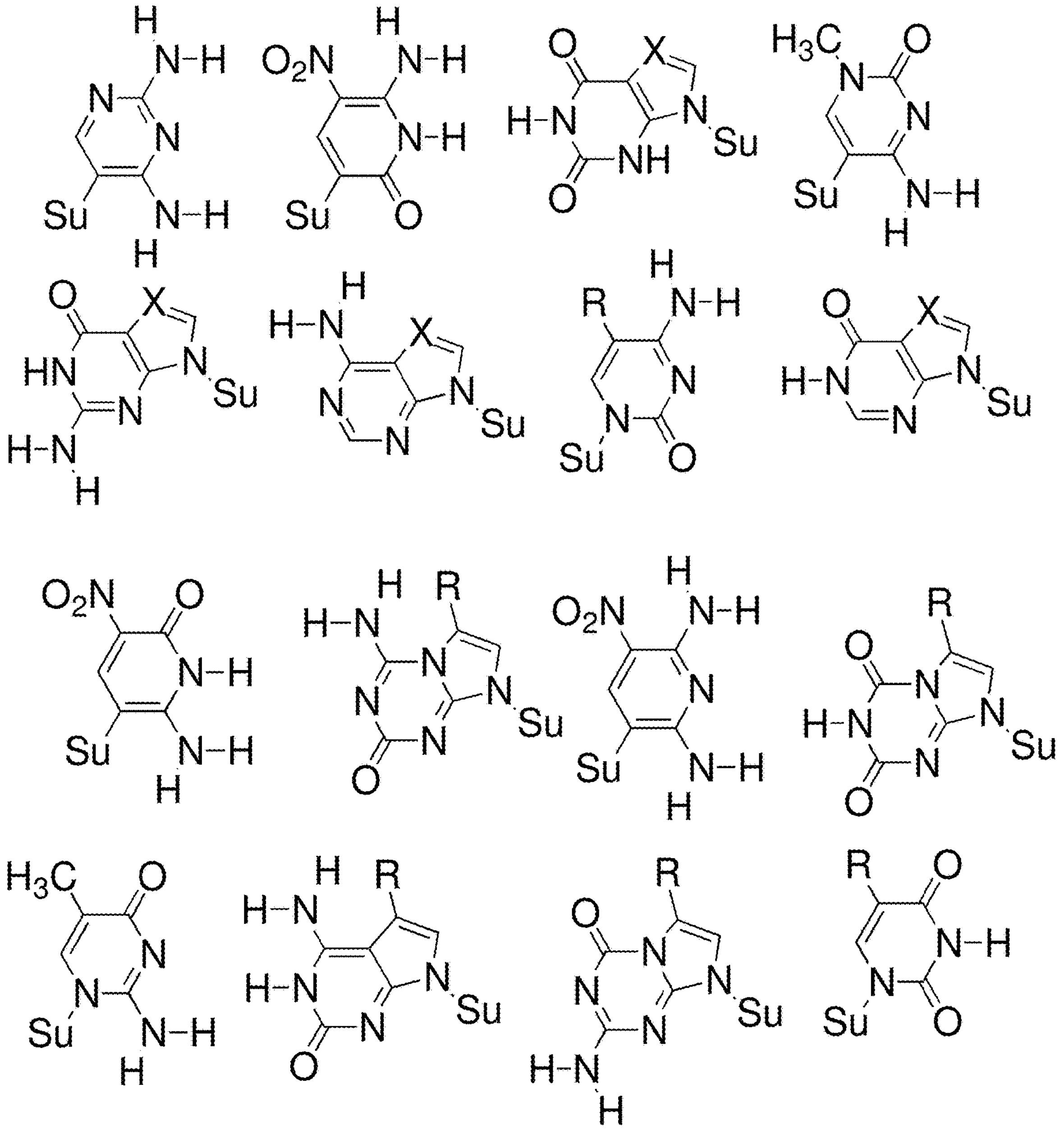

FIG. 6. Structures of the standard and non-standard 3'-aminoxytriphosphates of the instant invention, where Su indicates the point of attachment of the heterocycle to the sugar, R is either H, $CH_3$, or a functionalized side chain, and X is either N or C—R.

Figure 7:
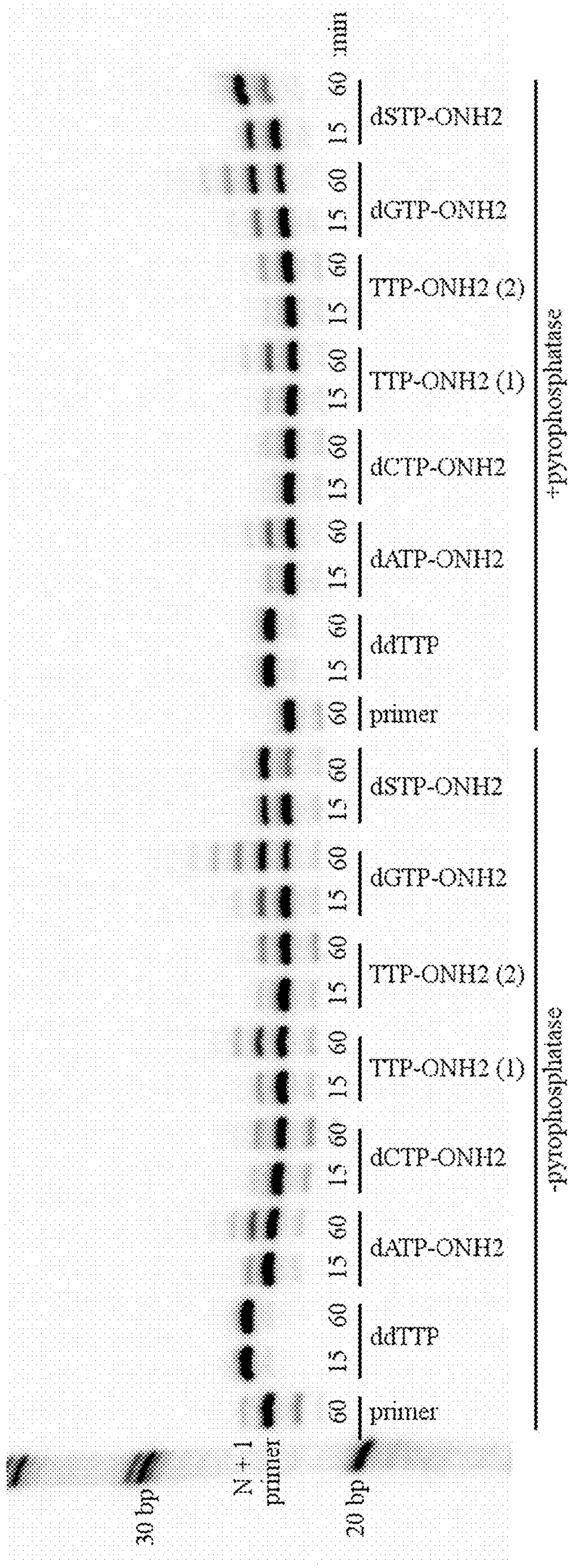

FIG. 7. PAGE (20%) of aminoxy reversibly terminated and irreversible triphosphate tested in terminal transferase reactions in the absence and presence of pyrophosphatase. Reactions were incubated for 15 and 60 min.

Figure 8:
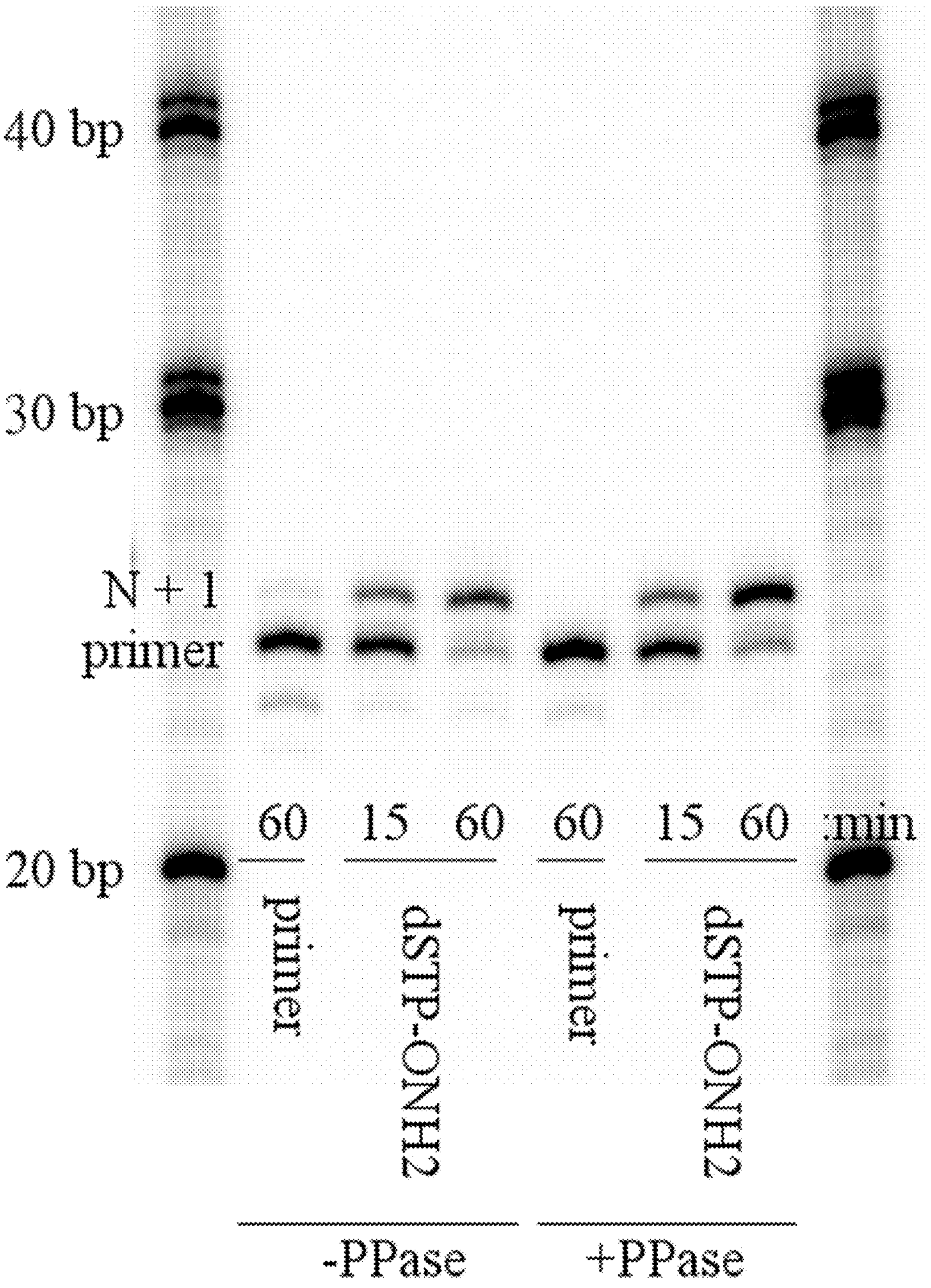

FIG. 8. PAGE (20%) of dSTP-$ONH_2$ without and with pyrophosphatase tested in terminal transferase reactions. Reactions were incubated for 15 and 60 min.

Figure 9:
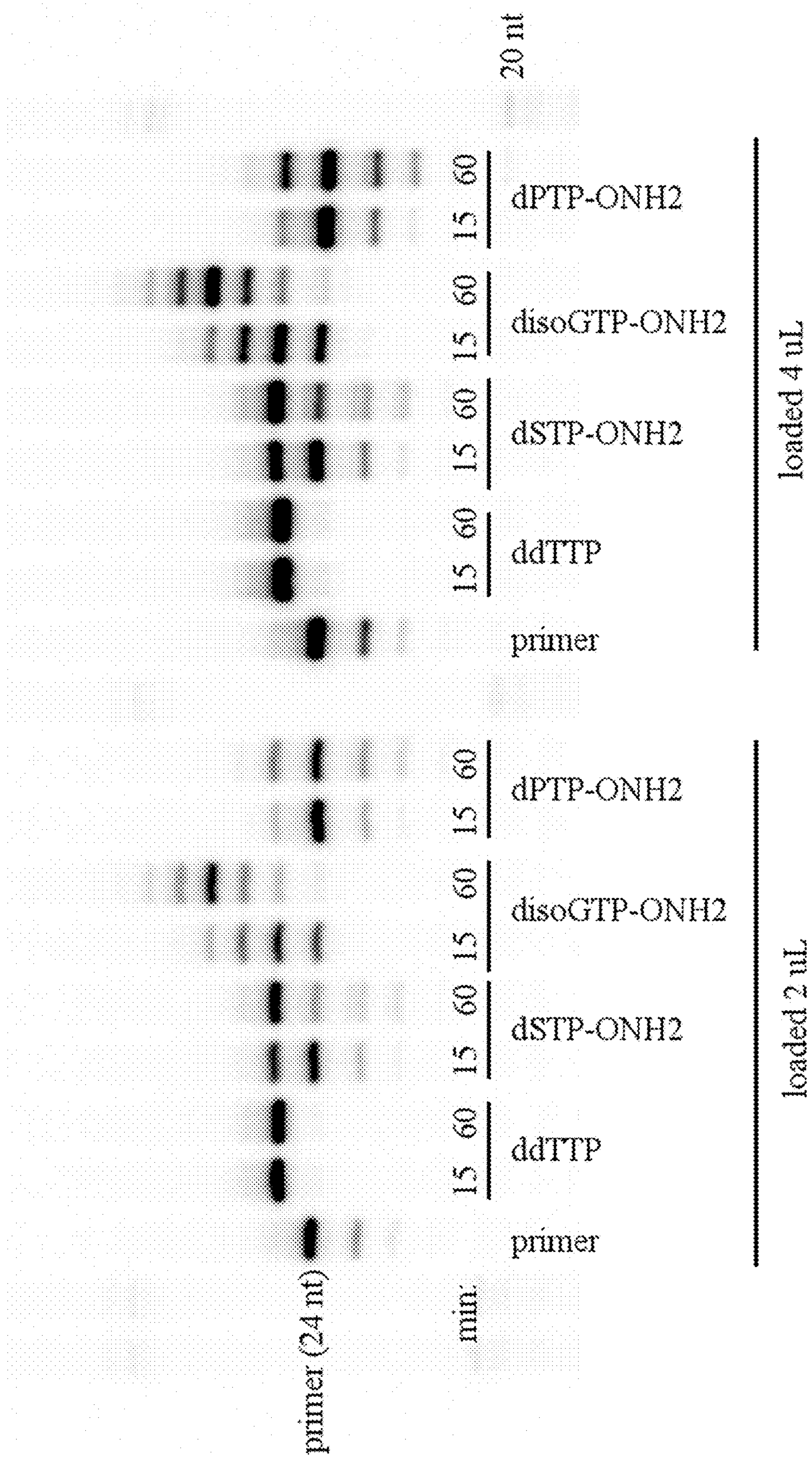

FIG. 9. PAGE (20%) of extension of primers using terminal transferase and AEGIS nucleotides "S" (a pyrimidine analog presenting an acceptor-acceptor-donor hydrogen bonding pattern), "B" (a purine analog presenting a donor-donor-acceptor hydrogen bonding pattern) and "P" (a purine analog presenting a donor-donor-acceptor hydrogen bonding pattern). aminoxy samples (tested in terminal transferase reactions. Reactions were incubated for 15 and 60 min. The tailing oligo is 24 bases long. Left panel was loaded 2 μL of samples; right panel was loaded 4 μL of samples.

FIG. 10. PAGE showing the ability of a variant of Taq DNA polymerase to incorporate dCTP-$ONH_2$ that was obtained by the art-described synthesis. [Hutter, D., Kim, M. J., Karalkar, N., Leal, N., Chen, F., Guggenheim, E., Visalakski, V., Olejnik, J., Gordon, S., Benner, S. A. (2010) Labeled nucleoside triphosphates with reversibly terminating aminoalkoxyl groups. *Nucleos. Nucleot. Nucl. Acids* 29, 879-895]. This establishes that the compounds can be incorporated by DNA polymerases. However, it also shows the inadequacy of prior art references to prevent the formation of ca. 3% of N+2 band resulting from trace (ca. 0.1%)

unblocked dCTP using a template with two consecutive G's. Reactions were incubated for 15 and 60 min.

DETAILED DESCRIPTION OF THE INVENTION

As noted in the description of the prior art, two types of processes benefit from the ability to extend a DNA molecule by just a single nucleotide. In the first type, the extension of the primer is untemplated. In this class of process, the invention disclosed here involves contacting a DNA primer oligonucleotide in an appropriate buffer with an enzyme known as terminal deoxynucleotide transferase (TdT, or simply terminal transferase). Terminal transferase was discovered many years ago in calf thymus as an enzyme that adds nucleoside triphosphates to the 3'-end of an oligonucleotide in an untemplated fashion. Some key references, which are incorporated herein by citation, are:

(a) Roychoudhury, R., Jay, E., Wu, R. (1976) *Nucl. Acids Res.* 3, 101-116. (b) Tu, C. P., Cohen, S. N. (1980) *Gene.* 10, 177-183. (c) Boule, J. B., Rougeon, F., Papanicolaou, C. (2001) *J. Biol. Chem.* 276, 31388-31393.

For standard nucleotides, defined as those that have standard nucleobases such as adenine, guanine, cytosine, and thymine, data disclosed in U.S. Pat. No. 8,034,923 show that terminal transferases accept triphosphates having a 3'-$ONH_2$ group. The presently preferred terminal deoxynucleotidyl transferase (TdT) prefers DNA as an oligonucleotide substrate. Single ribonucleotide addition is seen with the native enzyme a slower rate. The presently preferred TdT is the enzyme that is commercially available, sold by New England Biolabs or Promega, or the analogous enzyme obtained from other mammalian thymus glands. Most preferred is a TdT or one of its variants containing 1-3 amino acid replacements obtained via recombinant DNA technology. However, U.S. Pat. No. 8,034,923 does not constitute anticipatory prior art as it does not disclose triphosphates that are free of hydroxylamine.

The importance of freedom from hydroxylamine is disclosed in Application 154604475. In detail. U.S. Pat. No. 8,034,923 taught that hydroxylamine ($HONH_2$) should also be present in compositions containing triphosphates having a 3'-$ONH_2$ moiety. U.S. Pat. No. 8,034,923 taught that having hydroxylamine to compositions containing the triphosphates would scavenge adventitious aldehydes, or reversibly cleave the oximes should they be formed.

However, upon storage or even when freshly used, it was discovered that the 3'-$ONH_2$ unit decomposed to generate a triphosphate carrying a 3'-OH moiety in these prior art preparations. While not wishing to be bound by theory, the conversion of the 3'-nucleoside-O—$NH_2$ group to a 3'-nucleoside-OH appeared to arise from the presence of hydroxylamine, the same hydroxylamine taught in the art (including U.S. Pat. No. 8,034,923) to be used with those triphosphates.

Accordingly, Application 154604475 disclosed compositions of triphosphates that lacked hydroxylamine. These are the compositions used in the herein claimed processes, wherein a key limitation of the claims is the substantial absence of hydroxylamine, defined to be less than one micromolar, more preferably less than one nanomolar. Also claimed in Application 154604475 are inventive processes that deliver such compositions.

Also not disclosed in the prior art was the ability of such compositions to include triphosphates of nucleosides wherein the nucleobases or nonstandard. These are nucleobases other than adenine, guanine, cytosine, and thymine, but rather presented hydrogen bond patterns different from those found in the standard bases. These are shown in FIG. 5, and reduced to practice in the examples.

With respect to untemplated primer extension by just one nucleotide, the invention here comprises contacting an oligonucleotide, preferably an oligo-2'-deoxyribonucleotide, with a triphosphate, as disclosed in U.S. Pat. No. 8,034,923, carrying the 3'-$ONH_2$ moiety, in aqueous buffers where TdT operates. These buffers are well known in the art, and are provided in the examples below. The buffer may optionally contain divalent cobalt cation ($Co^{++}$), which may improve the ability of the terminal transferase to accept standard pyrimidine nucleoside triphosphates. However, with the aminoxy analogs, we have discovered that $Co^{++}$ does not improve the performance of TdT, at least in the buffers examined. Those buffers have preferable pH ranges from 7 to 8, but not outside pH 6 to 9. The preferable contact temperature is preferably between 25° C. and 40° C.

The utility of the instant invention arises from its ability to at a single nucleotide at a time.

This can be, for example, envisioned as a synthesis procedure, where an oligonucleotide having a defined, preselected, sequence is synthesized by contacting an immobilized primer with:

(a) a nucleoside triphosphate having a 3'-$ONH_2$ moiety and carrying the nucleobase of the desired first nucleotide in the preselected sequence, (b) incubating for a period of time to allow the single nucleotide addition to go substantially to completion, (c) washing the incubation mixture from the immobilized primer which now has additional nucleotide and a blocked 3'-end, (d) removing the 3'-aminoxy block, for example, by treating with buffered sodium nitrite following the procedure described in U.S. Pat. No. 8,034,923 (Benner, S. A., Hutter, D., Leal, N. A., Chen, F. Reagents for Reversibly Terminating Primer extension. U.S. Pat. No. 8,034,923), which is incorporated in its entirety by reference, and (e) repeating the cycle for each additional desired nucleotide in the preselected sequence.

For this and other applications where addition of just one nucleotide is desired, is preferred that the triphosphate having a 3'-$ONH_2$ moiety not be contaminated with triphosphates that have a standard, and extendable, 3'-OH group. As shown in the examples, TdT has a preference for the natural triphosphate having an extendable 3'-OH group. Indeed, TdT can be used to clean up preparations of triphosphates having a 3'-$ONH_2$ moiety by removing natural triphosphates having an extendable 3'-OH group. For other applications, this contamination is tolerable.

The most presently preferred triphosphates having a 3'-$ONH_2$ moiety are those prepared by the procedure disclosed in U.S. patent application Ser. No. 15/460,475, which is incorporated herein in its entirety by reference. These nucleoside triphosphates are substantially free of contaminating standard triphosphate, where "substantially" means that the preparation triphosphate carrying a 3'-O—$NH_2$ moiety contains less than 0.5 mole percent of the analogous triphosphate with a free 3'-OH group, more preferably less than 0.05 mole percent, and most preferably less than 0.005 mole percent, calculated relative to the triphosphate carrying a 3'-O—$NH_2$ moiety. Further, as taught in U.S. patent application Ser. No. 15/460,475, in addition to the standard nucleoside triphosphates shown in FIG. 5, the nucleoside might carry an unnatural nucleobase, selected from the structures shown in FIG. 6.

The art (for example Hutter et al. 2010) shows that aminoxy derivatives can be used in templated-directed oligonucleotide primer extension using DNA polymerases. Here, the oligonucleotide primer is presented with a template that contains a segment that is substantially complementary to the primer, where the primer is hybridized to the template, where the template has a single stranded segment 5'-distal to the segment where the primer is hybridized. The first nucleotide in this single stranded segment directs the polymerase to incorporate the 3'-aminoxy triphosphate that is singly added by the polymerase. This primer-template can be a hairpin.

The presently preferred polymerase is that from *Thermus aquaticus*, or a mutant thereof, as disclosed in Hutter et al. [2010]. However, neither Hutter et al. nor any other publication prior to the instant priority constitutes anticipatory prior art, as it does not disclose preparations of triphosphates that are free of hydroxylamine.

Optionally, the solution may also contain an alkoxylamine in addition to the alkoxylamine that is the triphosphate itself. Preferably, the additional dissolved alkoxylamine is a lower alkoxylamine such as methoxylamine. Preferably, the concentration of the alkoxylamine is between 10 and 50 micromolar, and is delivered in a sequence where the enzyme is first contacted with the primer, then contacted with the additional alkoxylamine, and then contacted with the triphosphates. This was discovered to prevent reaction of alkoxylamine with cytosine.

The solution to the stability problem opened up a wide range of hitherto unanticipated applications. For example, Karalkar and Benner solved the difficult problem of synthesizing the analogous ribonucleoside derivatives, where Z is OH or P-Me in the formula below (see U.S. patent application Ser. No. 16/887,951, filed 29 May 2020, incorporated in detail, including figures, legends, specification, abstract, examples, and claims].

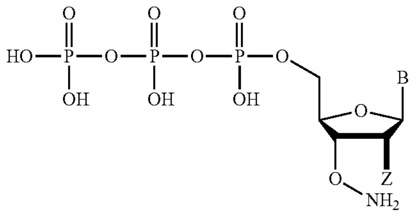

This extends the range of useful enzymes to DNA polymerases, reverse transcriptases, polynucleotide polymerases (e.g. polyA polymerase, polyU polymerase or their variants [Church, G. M., Wiegand, D. J., Kohnan, R. E., Kuru, E., Ricttichier, J., Conway, N. (2020) Enzymatic RNA Synthesis, WO/2020/077227 A2][Heinisch, T., Champion, E., Sune, E., Soskine, M. (2021) Template Free Enzymatic synthesis of polynucleotides using Poly(A) and Poly (U) polymerases, WO/2021/018919], and terminal deoxynucleotide transferases, and includes both templated and untemplated syntheses. This includes variants of these generated by site directed mutagenesis, directed evolution, screening, or other processes known to the artisans of diversity science. Also applicable are variants of polymerases (e.g., polymerase theta) [Pomerantz, R. T. (2016) Modification of 3' terminal ends of nucleic acids by DNA polymerase theta. WO2017075421A1], which provided processes for modifying the 3'-terminal ends of nucleic acids using DNA polymerase 0 terminal transferase activity.

EXAMPLES

Example 1

The ability of terminal transferase to add a 3'-aminoxy terminating triphosphate to oligonucleotides was discovered by a series of experiments. In these experiments, this oligonucleotide substrate was used.

```
dhSSP1:
                                          SEQ ID NO 1
5'-GCG TAA TAC GAC TCA CTA TGG ACG-3'
```

This oligonucleotide was 5'-labeled to give

5'-$^{32}$P-GCG TAA TAC GAC TCA CTA TGG ACG-3' which is SEQ ID NO 1) using OptiKinase and gamma-labeled radioactive ATP.

Two different buffers were used for the experiments that discovered the ability of terminal transferase to add a 3'-aminoxy terminating triphosphate to oligonucleotides. The "purine tailing buffer" contained 100 mM cacodylate buffer (pH 7.1), 2 mM $MnCl_2$, 0.1 mM DTT, 10 pmol of radiolabeled template (0.5 μM), 10 units of Terminal Transferase, and varying amounts of reversible terminating triphosphates ranging from 5 μM to 250 μM (as indicated on gel). The total volume was 20 μL.

The "pyrimidine tailing buffer" contained 100 mM cacodylate buffer (pH 7.1), 2 mM $CoCl_2$, 0.1 mM DTT, 10 pmol of radiolabeled template (0.5 μM), 10 units of Terminal Transferase, and varying amounts of reversible terminator triphosphates from 5 μM to 250 μM. Again, the total volume was 20 μL.

Samples were incubated at 37° C. for 1 hour. Then, the transferase reaction was terminated by heating at 70° C. for 10 min. Loading buffer 10 μL (98% formamide, 10 mM EDTA 1 mg/mL xylene cyanol and 1 mg/mL bromophenol blue) was added to each reaction mixture, and an aliquot containing 2 pmoles of products (4 μL) was resolved on 8% PAGE. An additional study was done testing just G-$ONH_2$ at 250 μM at 2, 5, 15, 30 and 60 min incubation at 37° C.

Data are shown in FIG. 1. Terminal transferase was able to incorporate all four nucleoside triphosphates containing the 3-$ONH_2$ block. In the purine buffer, dGTP-$ONH_2$ appears to be incorporated more easily than dATP-$ONH_2$. However even though this buffer is sold commercially to prefer standard purine nucleosides over pyrimidine nucleosides, dTTP-$ONH_2$ is still incorporated. However, in purine buffer, dCTP-$ONH_2$ is only slightly incorporated, and appears to inhibit the reaction at higher concentrations.

In the pyrimidine buffer, dGTP-$ONH_2$ and dATP-$ONH_2$ both are successfully incorporated, as is dTTP-$ONH_2$. dCTP-$ONH_2$ is perhaps incorporated better, but again appears to have inhibitory activity.

The results in FIG. 1 were obtained with triphosphates containing a small amount of 3-OH unblocked nucleoside triphosphates. The bands indicating incorporation of more than one nucleotide indicate this.

A time course for the incorporation of GTP-$ONH_2$ using TdT was then determined (FIG. 2). Nearly all of the primer has acquired an additional oligonucleotide) is seen. Thus, contacting oligonucleotide with the triphosphates is shown to be a way to incorporate the reversible terminator without the need of a template.

Example 2

The oligonucleotide primer used here is the same as in Example 1. The aminoxytriphosphates were prepared on a resin, as taught in U.S. patent application Ser. No. 15/460,475, but under a release procedure using $HONH_2$ elution, which did not minimize the presence of contaminating triphosphates with a free 3'-OH group. This shows the results of this procedure. Data are shown in FIG. 3. The lanes are as follows:

(a) The aminoxytriphosphate was synthesized on resin, with no Tris washes, and with immediate elution of the triphosphate with $HONH_2$ after synthesis (b) aminoxytriphosphate was synthesized on resin, with no Tris washes. The resin was then stored at room temperature overnight. Then, the triphosphate was eluted using $HONH_2$ and used.

(c) The aminoxytriphosphate was synthesized on resin, with three Tris washes overnight for one hour each. The aminoxytriphosphate was then eluted with $HONH_2$.

(d) The aminoxytriphosphate was synthesized on resin, which was then stored at room temperature overnight. The resin was then washed with Tris buffer (thrice, each for 1 hour). The aminoxytriphosphate was then eluted with $HONH_2$.

(e) The TdT extension was done with standard aminoxytriphosphate prepared in solution, a preparation that HPLC analysis showed contains ~0.5% 3'-OH.

(f) TdT extension was done with standard aminoxytriphosphate prepared in solution, following in situ deprotection of the acetoxime with $HONH_2$, with buffer concentrations as in (a-d)

(g) The same as in (f), but spiked with 2% TTP-OH containing a free 3'-hydroxyl group.

The TdT reaction was carried out as before with $^{32}P$-labeled primer (0.5 μM) in 1× in terminal transferase buffer (20 mM Tris-acetate, pH 7.9, 50 mM potassium acetate, 10 mM magnesium acetate, 1 mM dithiotheritol), 0.25 mM $CoCl_2$, 200 μM reversible terminator samples (a-f) and 10 Units of terminal deoxynucleotidyl transferase (TdT). Reactions were incubated at 37° C. for five and 50 min. Reactions were quenched by the addition of formamide quench buffer and were resolved on a 20% PAGE (FIG. 3).

Example 3

The TdT reaction was executed with dTTP-$ONH_2$ prepared as taught in U.S. patent application Ser. No. 15/460,475 using the same primer as above. Here, the aminoxytriphosphates were prepared by releasing TTP-$ONH_2$ from the resin using $MeONH_2$. Data are shown in FIG. 4.

(a) TTP-$ONH_2$, crude from resin synthesis, with $MeONH_2$ buffer (4.2 mM).

(b) TTP-$ONH_2$, pure from solution synthesis, with $MeONH_2$ buffer (5 mM).

(c) TTP-$ONH_2$, pure from solution synthesis, HPLC purified, no buffer $MeONH_2$, in pure water (4 mM).

(d) dGTP-$ONH_2$, pure from solution synthesis, HPLC purified, no $MeONH_2$ buffer, in pure water (5 mM)

As before, $^{32}P$ labeled primer (0.5 μM) in 1× in terminal transferase buffer (20 mM Tris-acetate, pH 7.9, 50 mM potassium acetate, 10 mM magnesium acetate, 1 mM dithiotheritol), with and without 0.25 mM $CoCl_2$, 200 μM reversible terminator samples (a-d) and 10 Units of terminal deoxynucleotidyl transferase (TdT). Control samples containing TTP and ddTTP were also tested. Reactions were incubated at 37° C. 5 and 60 min. Reactions were quenched by the addition of formamide quench buffer and were resolved on a 20% PAGE (FIG. 4).

Example 4

1) Terminal Transferase 3'-Tailing Studies

```
Primer dhSSP1
                                          SEQ ID NO 1
5'-GCG TAA TAC GAC TCA CTA TGG ACG-3'
```

| terminator | purity (at 260 nm) |
|---|---|
| dATP-$ONH_2$ | 67% |
| dCTP-$ONH_2$ | 74% |
| TTP-$ONH_2$ | 78% |
| TTP-$ONH_2$ in $dH_2O$ | |
| dGTP-$ONH_2$ | 76% |
| dSTP-$ONH_2$ | |

Radiolabeled $\gamma^{32}P$ dhSSP1 (0.5 μM) in 1× in terminal transferase buffer (20 mM Tris-acetate, pH 7.9, 50 mM potassium acetate, 10 mM magnesium acetate, 1 mM dithiotheritol), 0.25 mM $CoCl_2$, 200 μM reversible terminator samples or irreversible terminator and 0.5 U/μL of terminal deoxynucleotidyl transferase (TdT) without and with the addition of pyrophosphatase (0.05 Units in 20 μL reaction). Reactions were incubated at 37° C. 15 and 60 min. As a control, primer samples contained terminal transferase but lacked the addition of triphosphate. Reactions were quenched by the addition of formamide quench buffer and were resolved on a 20% PAGE (FIG. 7). Another gel was run to resolve the dSTP-$ONH_2$ queried samples (FIG. 8).

Separately, a reaction was run with radiolabeled $\gamma^{32}P$ dhSSP1 (0.1 μM) in 1× in terminal transferase buffer (20 mM Tris-acetate, pH 7.9, 50 mM potassium acetate, 10 mM magnesium acetate, 1 mM dithiothreitol), 0.25 mM $CoCl_2$, 200 μM reversible terminator samples or irreversible terminator and 1 U/μL of terminal deoxynucleotidyl transferase TdT). Reactions were incubated at 37° C. 15 and 60 min. As a control, primer samples contained terminal transferase but lacked the addition of triphosphate. Reactions were quenched by the addition of formamide quench buffer and were resolved on a 20% PAGE (FIG. 9).

Example 5

This is extracted from a prior art reference [Hutter, D., Kim, M. J., Karalkar, N., Leal, N., Chen, F., Guggenheim, E., Visalakski, V., Olejnik, J., Gordon, S., Benner, S. A. (2010) Labeled nucleoside triphosphates with reversibly terminating aminoalkoxyl groups. *Nucleos. Nucleot. Nucl. Acids* 29, 879-895]. This shows that 3'-aminoxy triphosphates are incorporated by DNA polymerases in template-directed processes, with primer, control template, and test template below. It also shows the inadequacy of prior art references to prevent formation of ca. 3% of N+2 band resulting from trace (ca. 0.1%) unblocked dCTP using a template with two consecutive G's. Reactions were incubated for 15 and 60 min. Results are shown in FIG. 10.

SEQ ID NO 2
5'-GCG TAA TAC GAC TCA CTA TGG ACG P1

-continued

SEQ ID NO 3
CGC ATT ATG CTG AGT GAT ACC TGC AAT GTG CTT CTT CTG-5' Template A

SEQ ID NO 4
CGC ATT ATG CTG AGT GAT ACC TGC GGT GTG CTT CTT CTG-5' Template G

What is claimed is:

1. A process that adds to an oligonucleotide primer a single nucleotide that has a 3'-$ONH_2$ moiety instead of a 3'-OH moiety, wherein said process comprises contacting an oligonucleotide primer in an aqueous buffered solution with an enzyme having terminal transferase activity and a compound having the structure:

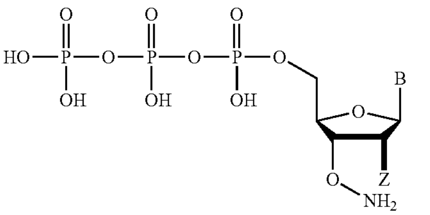

or one of its ionized forms, wherein Z is either H, OH, or $OCH_3$, B is a heterocycle selected from the group consisting of

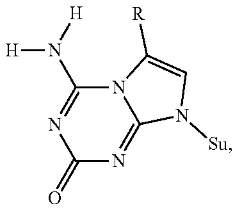
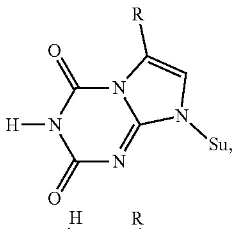
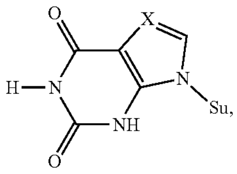
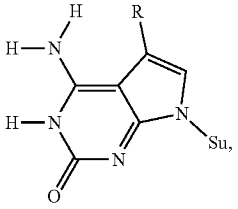
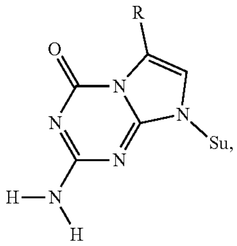
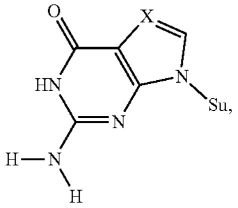
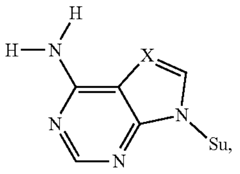
and
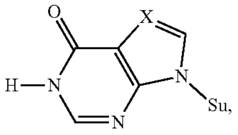

wherein Su indicates the point of attachment of the heterocycle to the sugar, R is either H, $CH_3$, or a functionalized side chain, and X is N, and wherein the concentration of hydroxylamine in said aqueous buffered solution that is less than 1 micromolar.

2. The process of claim 1, wherein said solution also contains additional dissolved alkoxylamine.

3. The process of claim 2, wherein said heterocycle B is selected from the group consisting of thymine, uracil, cytosine, guanine, adenine, and isocytosine.

4. The process of claim 2, wherein said heterocycle B is selected from the group consisting of thymine and isocytosine.

5. The process of claim 2, wherein appended to heterocycle B is a linker that comprises either a disulfide moiety or a 1,2-diol moiety.

6. The process of claim 2, wherein said heterocycle is

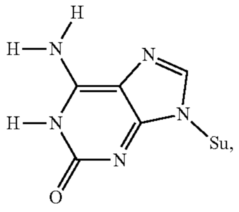

and wherein Su indicates the point of attachment of the heterocycle to the sugar.

7. The process of claim 2, wherein said heterocycle is

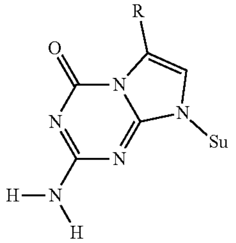

wherein Su indicates the point of attachment of the heterocycle to the sugar, and R is either H, $CH_3$, or a functionalized side chain.

8. The process of claim 2, wherein the concentration of the dissolved alkoxylamine is between 10 and 50 micromolar, and is delivered in a sequence where the enzyme is first contacted with the primer, then contacted with the additional alkoxylamine, and then contacted with the triphosphates.

9. The process of claim 2, wherein said enzyme is terminal deoxynucleotide transferase.

10. The process of claim 2, wherein said enzyme is a DNA polymerase, an RNA polymerase, a polyA polymerase, polyU polymerase, or a terminal transferase, and said oligonucleotide is hybridized to a template oligonucleotide.

11. The process of claim 1, wherein said heterocycle B is selected from the group consisting of thymine, uracil, cytosine, guanine, adenine, and isocytosine.

12. The process of claim 1, wherein said heterocycle B is selected from the group consisting of thymine and isocytosine.

13. The process of claim 1, wherein appended to heterocycle B is a linker that comprises either a disulfide moiety or a 1,2-diol moiety.

14. The process of claim 1, wherein said heterocycle is

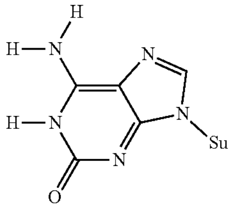

and wherein Su indicates the point of attachment of the heterocycle to the sugar.

15. The process of claim 1, wherein said heterocycle is

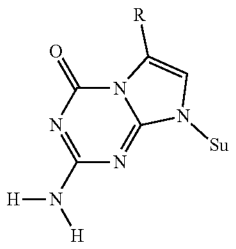

wherein Su indicates the point of attachment of the heterocycle to the sugar, and R is either H, $CH_3$, or a functionalized side chain.

16. The process of claim 1, wherein said enzyme is terminal deoxynucleotide transferase.

17. The process of claim 1, wherein said enzyme is a DNA polymerase, an RNA polymerase, a polyA polymerase, polyU polymerase, or a terminal transferase, and said oligonucleotide is hybridized to a template oligonucleotide.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: synthetic

<400> SEQUENCE: 1
gcgtaatacg actcactatg gacg 24

<210> SEQ ID NO 2
<211> LENGTH: 24
<212> TYPE: DNA
<213> ORGANISM: Artificial Sequence
<220> FEATURE:
<223> OTHER INFORMATION: synthetic

<400> SEQUENCE: 2
gcgtaatacg actcactatg gacg 24

<210> SEQ ID NO 3
<211> LENGTH: 39
<212> TYPE: DNA
<213> ORGANISM: Artificial Sequence
<220> FEATURE:
<223> OTHER INFORMATION: synthetic

<400> SEQUENCE: 3
gtcttcttcg tgtaacgtcc atagtgagtc gtattacgc 39

<210> SEQ ID NO 4
<211> LENGTH: 39
<212> TYPE: DNA
<213> ORGANISM: Artificial Sequence
<220> FEATURE:
<223> OTHER INFORMATION: synthetic

<400> SEQUENCE: 4
gtcttcttcg tgtggcgtcc atagtgagtc gtattacgc 39